United States Patent [19]

Gonzalez

[11] Patent Number: 5,762,498
[45] Date of Patent: Jun. 9, 1998

[54] DENTAL DRILL BIT

[76] Inventor: Arnaldo Gonzalez, c/o Walter A. Hass, 79 Haven Ave., Ste. 16, New York, N.Y. 10032

[21] Appl. No.: 665,485

[22] Filed: Jun. 18, 1996

[51] Int. Cl.[6] .................................................. A61C 3/02
[52] U.S. Cl. ............................................................. 433/165
[58] Field of Search .................................. 433/165, 166, 433/85; 408/57, 59

[56] References Cited

U.S. PATENT DOCUMENTS

| | | | |
|---|---|---|---|
| 2,453,696 | 11/1948 | Brooks | 433/165 |
| 4,021,920 | 5/1977 | Kirschner et al. | 433/165 |
| 4,869,668 | 9/1989 | Seney | 433/85 |
| 5,069,620 | 12/1991 | Matsutani | 433/82 |
| 5,096,421 | 3/1992 | Seney | 433/82 |
| 5,098,293 | 3/1992 | Loof et al. | 433/165 |
| 5,261,818 | 11/1993 | Shaw | 433/165 |
| 5,275,558 | 1/1994 | Seney | 433/82 |
| 5,433,604 | 7/1995 | Landgraf | 433/82 |
| 5,435,722 | 7/1995 | Mandell | 433/165 |
| 5,569,035 | 10/1996 | Balfour et al. | 433/165 |

Primary Examiner—Nicholas D. Lucchesi

[57] ABSTRACT

An improved dental drill bit (10) for use in a dental drill (18) having a short drill bit tip (12) which has a drill bit tip point (12A) positioned at an upper most distal end. A drill bit tip bottom (12B) is positioned at an opposite distal end to the drill bit tip point (12A). At least one drill bit tip plateau (12CA, 12CB) extends from the drill bit tip bottom (12B) to the drill bit tip point (12A). At least one drill bit tip groove (12DA, 12DB) extends from the drill bit tip bottom (12B) to the drill bit tip point (12A). A drill bit tip leading edge (12E) is formed between the at least one drill bit tip plateau (12CA, 12CB) and the at least one drill bit tip groove (12DA, 12DB). A base (14) comprises an upper base (14A) securely connected to a lower base (14B) having a middle base (14C) therebetween. The upper base (14A) is securely connected to the drill bit tip bottom (12B). An elongated shaft (16) has a shaft top (16A) securely connected to a shaft bottom (16B) having a shaft middle (16C) therebetween. The shaft top (16A) is securely connected to the lower base (14B).

4 Claims, 6 Drawing Sheets

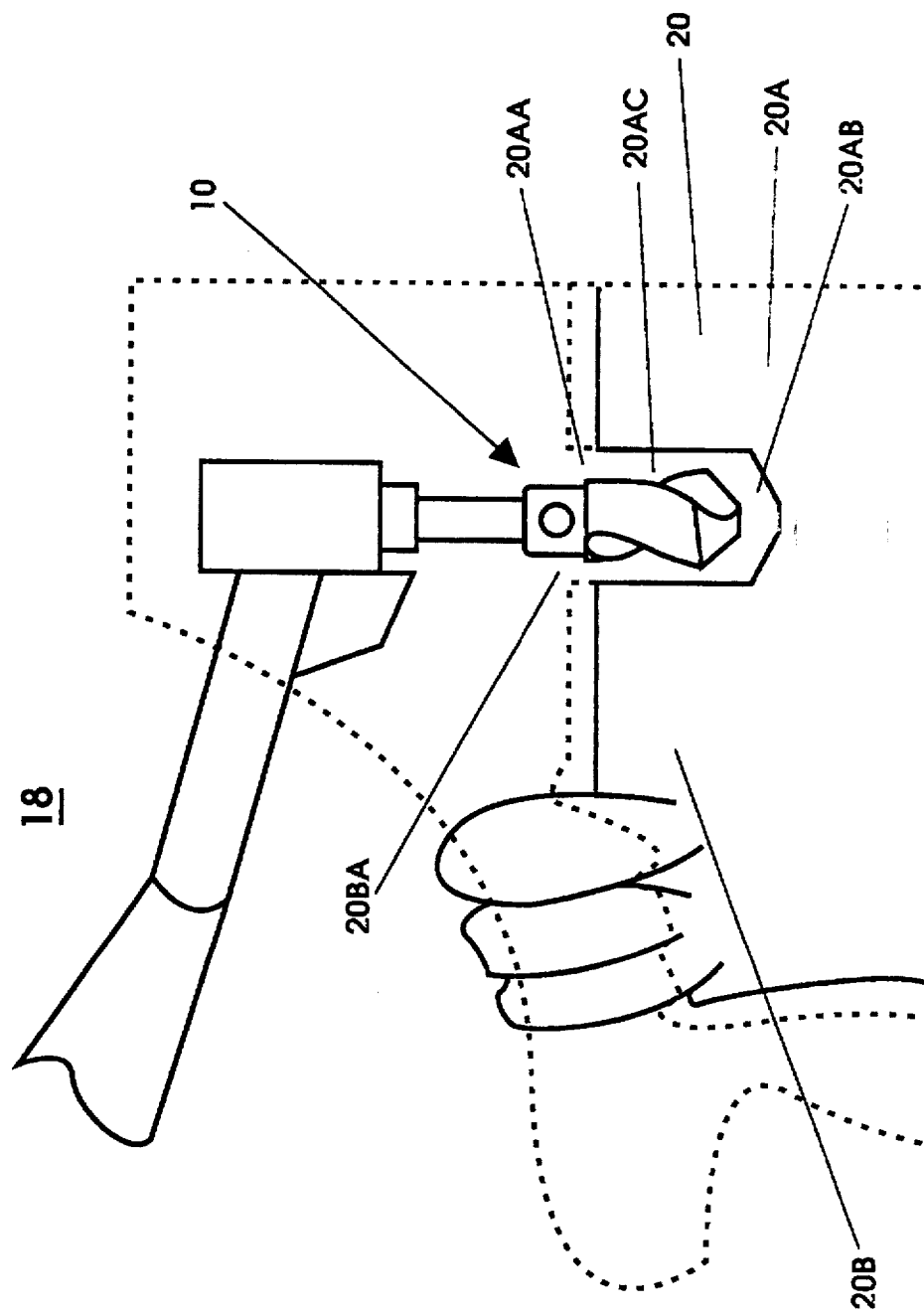

1

DENTAL DRILL BIT

BACKGROUND OF THE INVENTION

1. Field of the Invention

The present invention relates to dental drill bits. More particularly, the present invention relates to dental drill bits for root form implants.

2. Description of the Prior Art

Dental drill bits are well known in the art. At present, all dental drill bits have an elongated drill bit tip and a short shaft or no shaft. The prior art drill bits produce excessive amounts of heat during use which is primarily due to the elongated drill bit tip. In addition, the elongated drill tip bit produces fluted drill holes during use which is undesirable when securing implants in place. In contrast, the present invention has a shortened drill bit tip and an elongated shaft which eliminates the undesirable qualities of the prior art.

Numerous innovations for dental drill bits have been provided in the prior art that are described as follows. Even though these innovations may be suitable for the specific individual purposes to which they address, they differ from the present invention as hereinafter contrasted.

In U.S. Pat. No. 5,433,604, titled Medical Instrument Having an Internally Cooled Tool, a medical instrument, particularly a dental instrument has a head housing with a chucking arrangement for gripping an internally-cooled tool. In order to assume an optimum transfer of coolant from a delivery channel into an internal channel of the tool, an exit opening of the delivery channel is arranged opposite the admission opening of the tool in a no contact fashion at the end of the tool being gripped. To prevent leakage, sealing gaps are provided between the moving parts in the head housing and compressed air charged into these sealing gaps under a higher pressure in comparison to the pressure of the coolant.

The patented invention differs from your invention because the patented invention is a head housing with a chucking arrangement for gripping an internally-cooled tool. It is not a bur. Your invention is a bur having a central cooling channel with diametrically opposed exit ports near but above the bit portion of the bur.

In U.S. Pat. No. 5,275,558, titled Dental Handpiece, Bur Mount Operating System, a dental handpiece provided with a handle and a head on one end thereof in which a turbine rotates at high speeds and accommodates a cutting bur having an axial through opening to direct a preferably hygienic coolant directly through the cutting end of the bur, while the opposite end of the bur, on the interior of the head, is highly polished and absolutely flat for rotating engagement with one surface of a rotary liquid seal including a seal member of very hard substance in combination being housed within a recess extending upwardly in a push button on the head or other finger-operated bur release mechanism an the head and having coaxial fluid openings communicating axially with the through openings in the bur and fluid passage in the handle, the fluid preferably consists of one or more of several chair side selectable pharmaceutical ingredients added to a coolant for discharge into a cavity being cut in a tooth by the handpiece.

The patented invention differs from your invention because the patented invention is a dental handpiece provided with a handle and a head on one end thereof in which a turbine rotates at high speeds and accommodates a cutting bur. It is not a bur but functions to hold a bur. Your invention is a bur having a central cooling channel with diametrically opposed exit ports near but above the bit portion of the bur. The shaft is of smaller diameter than the bit end which provides for exhausting debris and cools the surrounding tooth or bone area.

In U.S. Pat. No. 5,489,208, titled Dental Bur with Liquid-Cooled Tip, according to the invention, there is providing an elongated liquid-cooled dental bur having a long direction, a proximal part adapted to be inserted into a drive device connected with a source of cooling fluid, a distal part having a cutting tip, a first channel in the proximal part fluidly communicating with a source of cooling fluid an at least one orifice extending from the first channel directed at the cutting tip for directing a spray of cooling fluid at the cutting tip, a cutting tip outer surface, a second channel fluidly communicating with the source of cooling fluid and extending longitudinally through the distal part and into the cutting tip, a discharge port extending through the tip outer surface for cooling the cutting tip. The dental bur may further include a collar radially extending from the proximal part having a circumference, wherein the orifice is disposed in the collar proximal to the circumference, and wherein the collar has an end surface disposed transversely to the long direction facing the distal part, and the orifice is disposed in the end surface. The cutting tip has a substantially cylindrical shape or a tapered shape.

The patented invention differs from your invention because the patented invention is an elongated liquid-cooled dental bur having a long direction, a proximal part adapted to be inserted into a drive device connected with a source of cooling fluid, a distal part having a cutting tip. The patented invention bur has a cylindrical shaft of substantially constant diameter through to the cutting end. The cooling fluid exits centrally from the tip and must flow around the cutting head to remove debris. The constant diameter shaft does not have the advantage of cooling the surrounding bone material as does your invention. Your invention is a bur having a central cooling channel with diametrically opposed exit ports near but above the bit portion of the bur. The shaft is of smaller diameter than the bit end which provides for exhausting debris and cools the surrounding tooth or bone area.

In U.S. Pat. No. 5,435,722, titled Dental Bur with Liquid Cooled Tip, according to the invention there is provided an elongated liquid-cooled dental bur having a long direction, a proximal part adapted to be inserted into a drive device connected with a source of cooling fluid, a distal part having a cutting tip, a first channel in the proximal part fluidly communicating with the source of cooling fluid and at least one orifice extending from the first channel directed at the cutting tip, and further including a collar radially extending from the proximal part having a circumference, wherein the orifice is disposed in the collar proximal to the circumference, and wherein in the collar has an end surface disposed transversely to the long direction facing the distal part, and the orifice is disposed in the end surface. The distal part is preferably removably secured to the collar, for removal and replacement of worn cutting tips. The distal part preferably fits into an axial bore in the screw. The cutting tip may be substantially spherically shaped.

The patented invention differs from your invention because the patented invention is an elongated liquid-cooled dental bur having a long direction, a proximal part adapted to be inserted into a drive device connected with a source of cooling fluid, a distal part having a cutting tip. The patented invention bur has a cylindrical shaft of substantially constant diameter through to the cutting end. The cooling fluid exits centrally from the tip and must flow around the cutting head to remove debris. The constant diameter shaft does not have the advantage of cooling the surrounding bone material as does your invention. Your invention is a bur having a central cooling channel with diametrically opposed exit ports near but above the bit portion of the bur. The shaft is of smaller diameter than the bit end which provides for exhausting debris and cools the surrounding tooth or bone area.

In U.S. Pat. No. 5,069,620, titled Dental Handpiece, invented by Kahji Matsutani, a dental handpiece includes an arm, and hollow head formed on the distal end of the arm. A dental bur is held in the head by a chucking means being adapted to force cooling fluid through the hollow central core of the burr. The cooling fluid exits the end of the bur and the burr is conical in shape.

The patented invention differs from your invention because the patented invention is a dental handpiece includes an arm, and hollow head formed on the distal end of the arm has a chuck adapted to accept standard burs. Your invention is a bur having a central cooling channel with diametrically opposed exit ports near but above the bit portion of the bur. The shaft is of smaller diameter than the bit end which provides for exhausting debris and cools the surrounding tooth or bone area.

In U.S. Pat. No. 5,275,558, titled Dental Handpiece, Bur Mount Operating System, a dental handpiece includes an arm, and hollow head in which a turbine rotates at high speed. A dental bur is held in the head by a chucking means being adapted to force cooling fluid through the hollow central core of the burr. No description of a bur is given as the patented invention is adapted to accept standard centrally cooled burs.

The patented invention differs from your invention because the patented invention is a dental handpiece includes an arm, and hollow head formed on the distal end of the arm has a chuck adapted to accept standard burs. Your invention is a bur having a central cooling channel with diametrically opposed exit ports near but above the bit portion of the bur. The shaft is of smaller diameter than the bit end which provides for exhausting debris and cools the surrounding tooth or bone area.

In U.S. Pat. No. 5,096,421, titled Dental Bur Cooling System, an air-turbine type dental handpiece in which the handle has separate passages for air and water under pressure respectively to drive the turbine to rotate a bur and furnish cooling fluid to the bur. The bur has a central hollow shaft which channels the cooling fluid out the end portion of the bur.

The patented invention differs from your invention because the patented invention is a dental handpiece includes an arm, and hollow head formed on the distal end of the arm has a chuck adapted to accept standard burs. Your invention is a bur having a central cooling channel with diametrically opposed exit ports near but above the bit portion of the bur. The shaft is of smaller diameter than the bit end which provides for exhausting debris and cools the surrounding tooth or bone area.

Numerous innovations for dental drill bit tips have been provided in the prior art that are adapted to be used. Even though these innovations may be suitable for the specific individual purposes to which they address, they would not be suitable for the purposes of the present invention as heretofore described.

SUMMARY OF THE INVENTION

The present invention relates to Dental drill bits. More particularly, the present invention relates to dental drill bits for root form implants. Unlike the prior art dental drill bits having an elongated drill bit tip and a shortened shaft, the present invention has a short drill bit tip and an elongated shaft.

The types of problems encountered in the prior art are fluted drill holes and excessive heat.

In the prior art, unsuccessful attempts to solve this problem were attempted namely: producing dental drills which extrude pressurized water and/or air. However, the problem was solved by the present invention because the improved dental drill bit has a shortened drill bit tip and an elongated shaft. In addition, heat is further reduced by having at least one middle base opening.

Innovations within the prior art are rapidly being exploited in the field of "painless dentistry".

The present invention went contrary to the teaching of the art which teaches elongated drill bit tips in conjunction with cooling methods such as pressurized water and/or air.

The present invention solved a long felt need for a dental drill bit which eliminates or reduces fluting while drilling as well as production of excessive heat.

The present invention produced unexpected results namely: implants grafted more readily to holes drilled with the present invention because trauma to the area was reduced.

Accordingly, it is an object of the present invention to provide an improved dental drill bit.

More particularly, it is an object of the present invention to provide an improved dental drill bit comprising a drill bit tip securely fastened to a base which is securely fastened to a shaft.

In keeping with these objects, and with others which will become apparent hereinafter, one feature of the present invention resides, briefly stated, in the drill bit tip having at least one drill bit tip plateau alternating in a circumferential configuration with at least one drill bit tip groove forming a drill bit tip leading edge therebetween.

When the drill bit tip is designed in accordance with the present invention, the at least one drill bit tip plateau and the at least one drill bit tip groove extends from a drill bit tip point at an upper distal end to a drill bit tip bottom at a lower distal end.

In accordance with another feature of the present invention, the base comprises an upper base fastened to a lower base having a middle base therebetween.

Another feature of the present invention is that the middle base further comprises at least one middle base opening which functions as a cooling means.

Yet another feature of the present invention is that the upper base is securely fastened to the drill bit tip bottom.

Still another feature of the present invention is that the shaft comprises a shaft top securely fastened to a shaft bottom having a shaft middle therebetween.

Yet still another feature of the present invention is that the shaft bottom further comprises a shaft bottom notch, a shaft bottom crescent, and a shaft bottom groove.

Still yet another feature of the present invention is that the shaft bottom crescent further comprises a shaft bottom crescent opening therein.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING 10-improved dental drill bit (10)
12-drill bit tip (12)
12A-drill bit tip point (12A)
12B-drill bit tip bottom (12B)
12CA-drill bit tip first plateau (12CA)
12CB-drill bit tip second plateau (12CB)
12DA-drill bit tip first groove (12DA)
12DB-drill bit tip second groove (12DB)
12E-drill bit tip leading edge (12E)
14-base (14)
14A-upper base (14A)
14B-lower base (14B)
14C-middle base (14C)
14CA-middle base opening (14CA)
16-shaft (16)
16A-shaft top (16A)
16B-shaft bottom (16B)
16BA-shaft bottom notch (16BA)
16BB-shaft bottom crescent (16BB)
16BBA-shaft bottom crescent opening (16BBA)
16BC-shaft bottom groove (16BC)
16C-shaft middle (16C)
18-dental drill (18)
20-person's jaw (20)
20A-person's jaw bone drill hole (20A)
20AA-person's jaw bone upper drill hole (20AA)
20AB-person's jaw bone lower drill hole (20AB)
20AC-person's jaw bone middle drill hole (20AC)
20B-person's gum (20B)
20BA-person's gum incision (20BA)

BRIEF DESCRIPTION OF THE DRAWING

FIG. 2 is a person's jaw bone drill hole having uniform thickness formed by the improved dental drill bit.

DESCRIPTION OF THE PREFERRED EMBODIMENT

Figure 1:
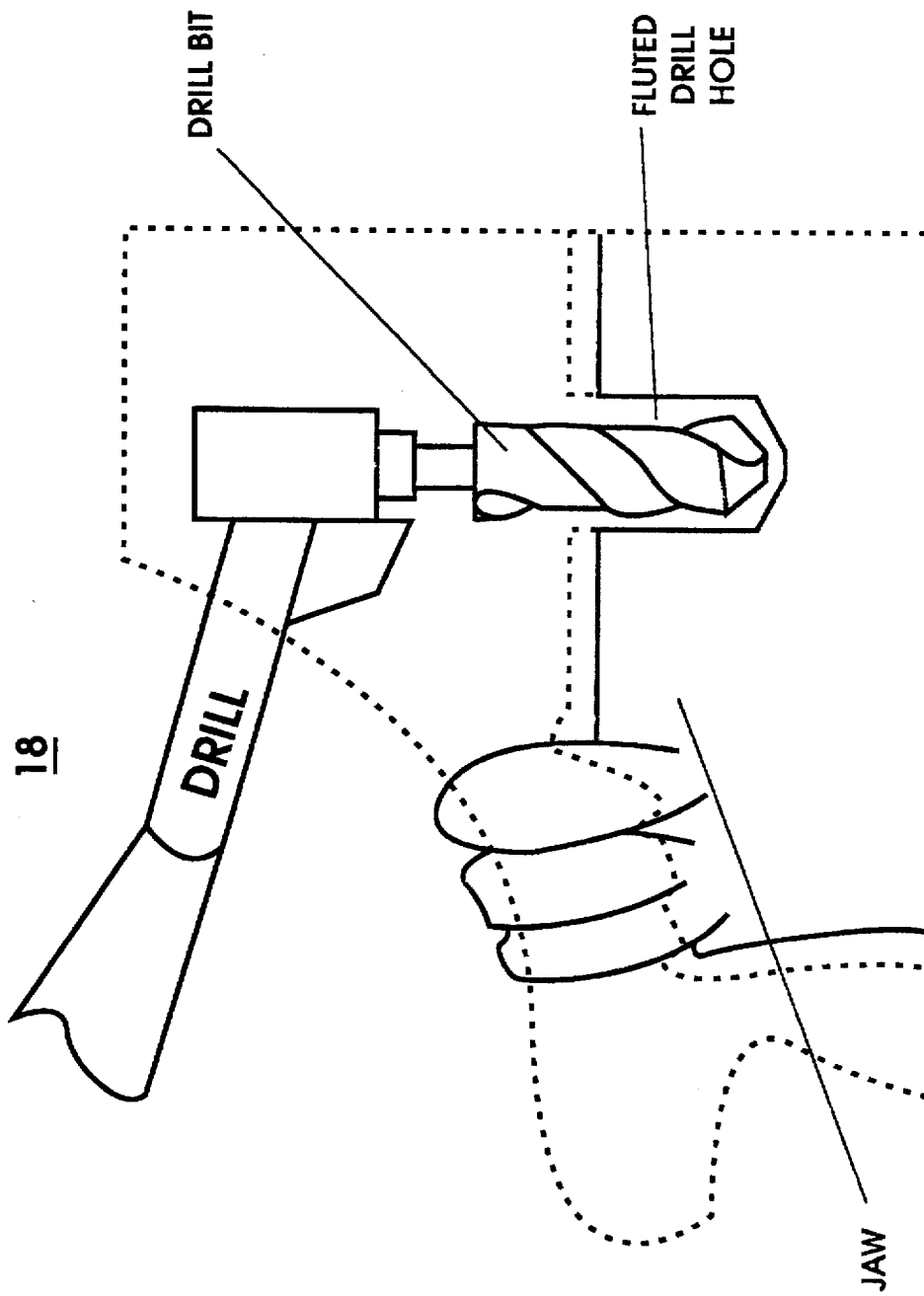
FIG. 1 is a partial cross-sectional side view of a prior art fluted drill hole formed by a prior art drill bit.

Firstly, referring to FIG. 1 which is a partial cross-sectional side view of a prior art fluted drill hole formed by a prior art drill bit. The prior art drill bits have a cutting edge extending from the drill to the drill tip point with a small shaft or no shaft. This arrangement is not desirable since the leading edge is extremely long which produces excessive heat which is extremely uncomfortable to a patient. It is further non-desirable to have a long cutting edge since when a dentist is drilling a hole in a person's jaw and moves the drill in a left-right and/or forward-backward direction, a fluted drill hole is formed in which an implant base does not affix as well as if the hole was uniform in size.

Referring to FIG. 2 which is a person's jaw bone drill hole (20A) having uniform thickness formed by the improved dental drill bit (10). The improved dental drill bit (10) has an elongated shaft (16) which is securely attached to a small drill bit tip (12) having a base (14) therebetween. The elongated shaft (16) prevents "fluting" of a person's jaw bone drill hole (20A) drilled within a person's jaw (20) because a drill bit tip leading edge (12E) is minimized in size. In addition, a minimized drill bit tip leading edge (12E) reduces heat which is produced during the drilling process. Furthermore, the elongated shaft (16) and minimized drill bit tip leading edge (12E) allows easy and rapid removal, by pneumatic means and/or hydromatic means, of bone particles produced during drilling. Prior to drilling, a person's gum (20B) is operated upon forming a person's gum incision (20BA). By utilizing the improved dental drill bit (10), a person's jaw bone drill hole (20A) is uniform in diameter having similarly sized person's jaw bone upper drill hole (20AA), person's jaw bone lower drill hole (20AB), and person's jaw bone middle drill hole (20AC) which contrasts the prior art drill bits which produce "fluted drill holes".

Figure 3A:
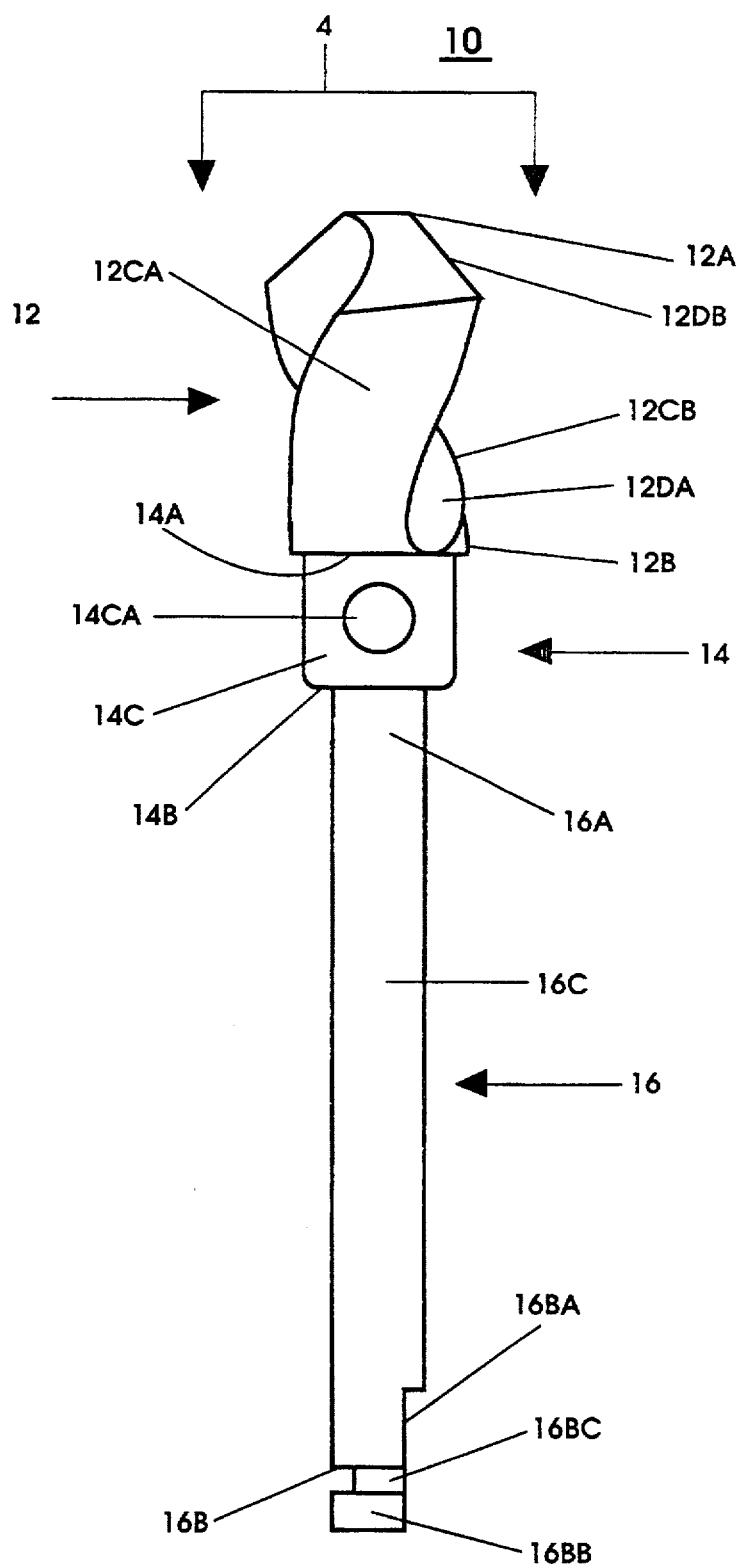
FIG. 3A is a side view of an improved dental drill bit exhibiting a middle base opening in the middle base.
Figure 3B:
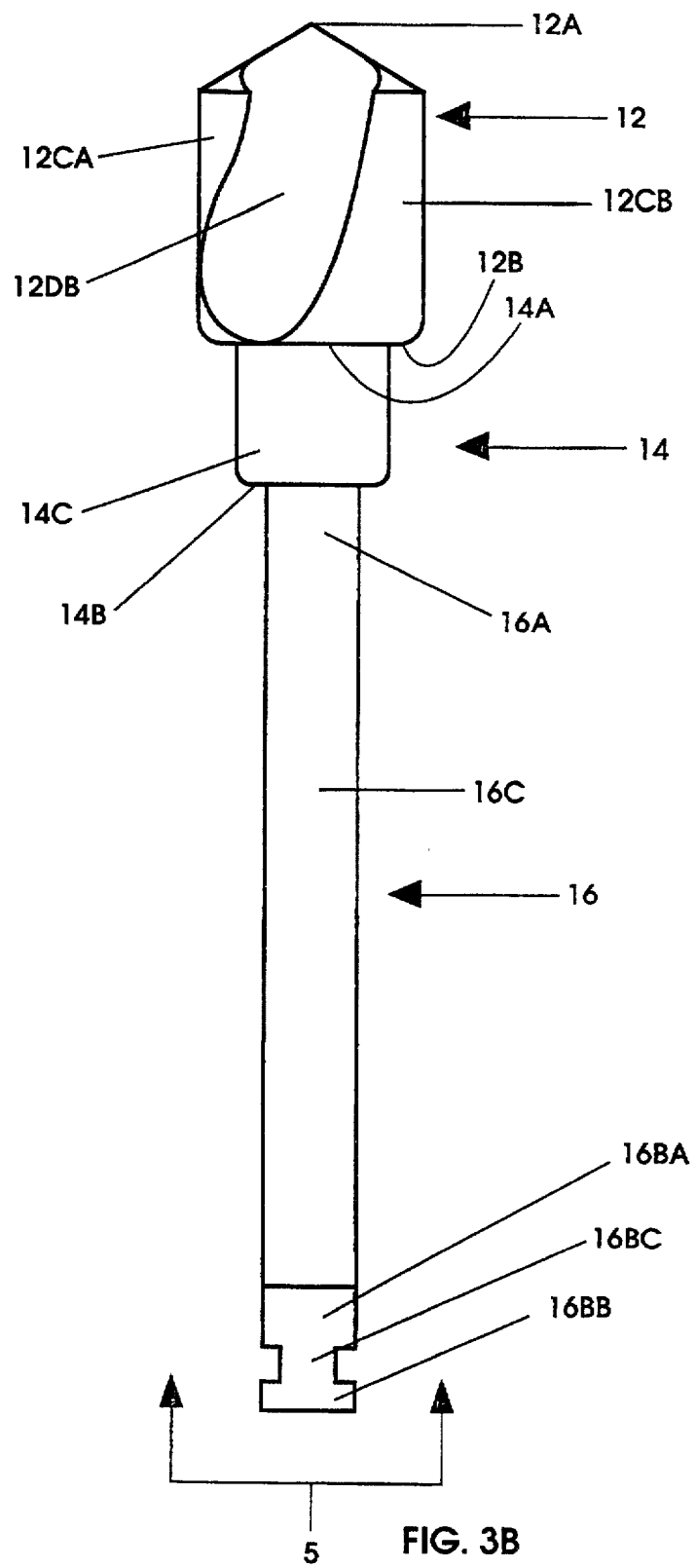
FIG. 3B is a ninety degree side view of an improved dental drill bit.
Figure 4:
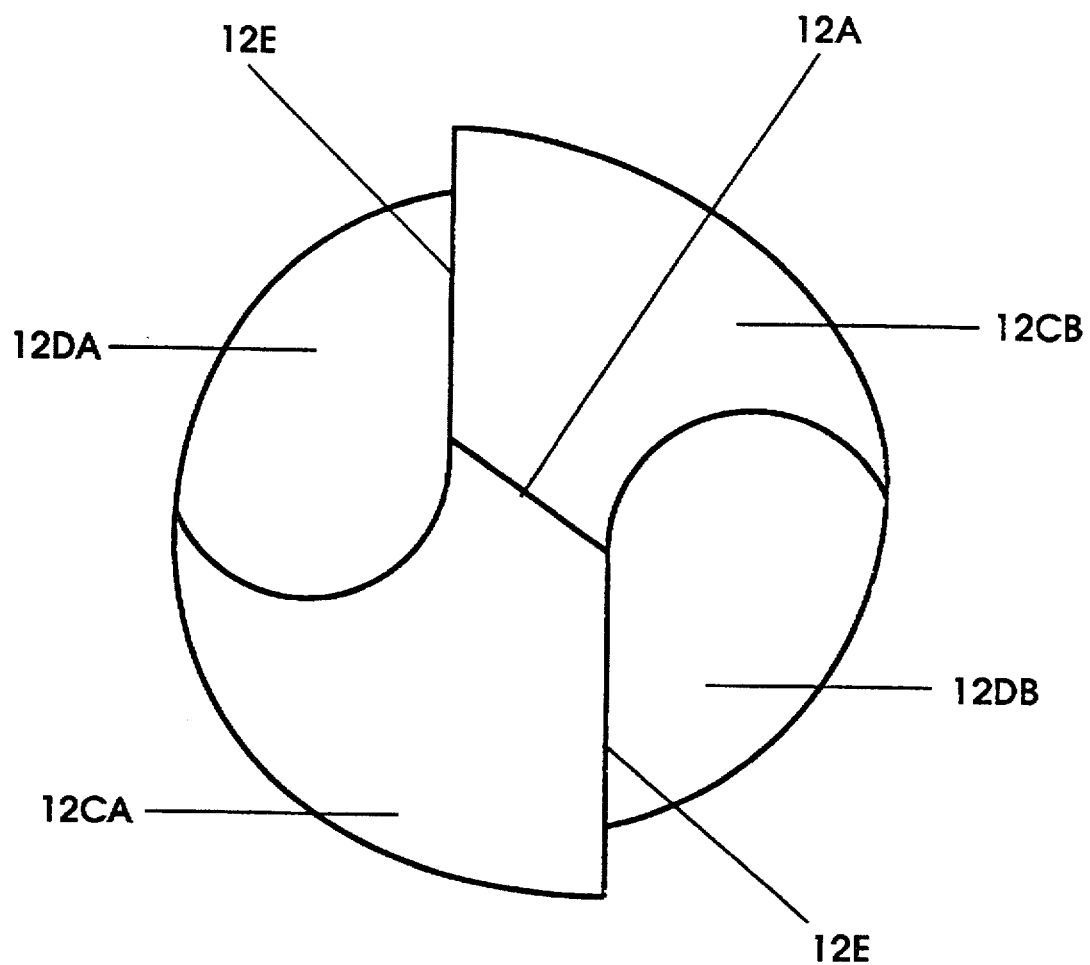
FIG. 4 is a top view of a drill bit tip.

Referring to FIG. 3A, FIG. 3B, and FIG. 4 which are a side view, a ninety degree side view and a top view of an improved dental drill bit (10), respectively, exhibiting a middle base opening (14CA) in the middle base (14C). The improved dental drill bit (10) has a drill bit tip (12) which comprises at least one drill bit tip plateau (12CA, 12CB) alternating circumferentially with at least one drill bit tip groove (12DA, 12DB). The at least one drill bit tip plateau (12CA, 12CB) and the at least one drill bit tip groove (12DA, 12DB) extend from a drill bit tip point (12A) to a drill bit tip bottom (12B). A drill bit tip leading edge (12E) is formed between the at least one drill bit tip plateau (12CA, 12CB) and the at least one drill bit tip groove (12DA, 12DB) which functions as a secondary cutting means. The drill bit tip point (12A) functions as a primary cutting means. The drill bit tip (12) is manufactured from a material selected from a group consisting of metal, metal alloy, plastic, plastic composite, ceramic, diamond, cubic zirconium, rubber, rubber composite and glass.

A base (14) is securely connected to the drill bit tip (12). The base (14) comprises an upper base (14A) which is securely fastened to the drill bit tip bottom (12B). The upper base (14A) is connected to a lower base (14B) having a middle base (14C) therebetween. The middle base (14C) preferably has at least one middle base opening (14CA) which functions to cool the base (14) and the drill bit tip (12) during use. The cooling occurs when pressurized water and/or air emanating from the dental drill (18) is forced through the at least one middle base opening (14CA). The base (14) is manufactured from a material selected from a group consisting of metal, metal alloy, plastic, plastic composite, ceramic, diamond, cubic zirconium, rubber, rubber composite and glass.

Figure 5:
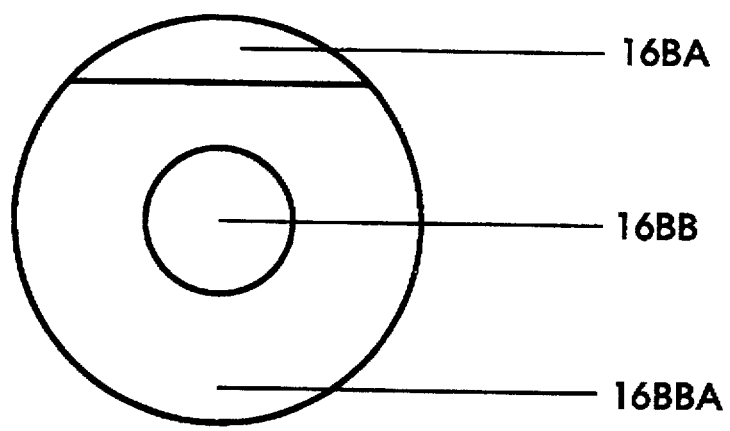
FIG. 5 is a bottom view of a shaft.

A shaft (16) is securely connected to the base (14). The shaft (16) functions as an attachment means to connect the drill bit tip (12) and base (14) to the dental drill (18). As compared to the prior art which had a short shaft or no shaft in conjunction with an elongated drill bit, the improved dental drill bit (10) has an elongated shaft and a short drill bit tip (12). The shaft (16) comprises a shaft top (16A) connected to a shaft bottom (16B) having a shaft middle (16C) therebetween. The shaft top (16A) is securely fastened to the lower base (14B). The shaft bottom (16B) functions as a secure attachment means connecting the shaft (16) to the dental drill (18). Referring to FIG. 5 which is a bottom view of a shaft (16). The shaft bottom (16B) comprises a shaft bottom notch (16BA) which functions as a primary fastening means by fitting into a complimentary notch-shaped socket in the dental drill (18). The shaft bottom (16B) further comprises a shaft bottom crescent (16BB) which functions as a secondary fastening means by fitting into a complimentary crescent-shaped socket in the dental drill (18). The shaft bottom (16B) further comprises a shaft bottom groove (16BC) which functions as a secondary alignment means by fitting into a complimentary groove-shaped protrusion in the dental drill (18). The shaft bottom crescent (16BB) further comprises a shaft bottom crescent opening (16BBA) which functions as a primary alignment means by fitting into a complimentary crescent opening-shaped protrusion (rod) in the dental drill (18).

It will be understood that each of the elements described above, or two or more together, may also find a useful application in other types of constructions differing from the type described above.

While the invention has been illustrated and described as embodied in an improved dental drill bit, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. An improved dental drill bit (10) comprising:
   A) a short drill bit tip (12) having a length less than three millimeters, the short drill bit tip (12) comprises:
      i) a drill bit tip point (12A) positioned at an upper distal end, the drill bit tip point (12A) functions as a primary cutting means,
      ii) a drill bit tip bottom (12B) positioned at an opposite distal end to the drill bit tip point (12A),
      iii) at least one drill bit tip plateau (12CA, 12CB) which extends from the drill bit tip bottom (12B) to the drill bit tip point (12A), and
      iv) at least one drill bit tip groove (12DA, 12DB) which extends from the drill bit tip bottom (12B) to the drill bit tip point (12A), a drill bit tip leading edge (12E) is formed between the at least one drill bit tip plateau (12CA, 12CB) and the at least one drill bit tip groove (12DA, 12DB), the drill bit tip leading edge (12E) functions as a secondary cutting means, the drill bit tip plateau (12CA, 12CA) comprises a similar cylindrical diameter to the drill bit tip bottom (12B);
   B) a base (14) which comprises an upper base (14A) securely connected to a lower base (14B) having a middle base (14C) therebetween, the upper base (14A) is securely connected to the drill bit tip bottom (12B), the base (14) functions to securely hold the drill bit tip (12), the middle base (14C) comprises at least one middle base opening (14CA) therethrough which functions as a cooling means for the drill bit tip (12) and the base (14), the base (14) comprises a smaller diameter than the cylindrical diameter of the drill bit tip plateau (12CA, 12CA) and the drill bit tip bottom (12B); and
   C) an elongated shaft (16) which comprises a shaft top (16A) securely connected to a shaft bottom (16B) having a shaft middle (16C) therebetween, the shaft top (16A) is securely connected to the lower base (14B), the shaft (16) functions as a means by which a dental drill (18) securely holds the improved dental drill bit (10).

2. The improved dental drill bit (10) as described in claim 1, wherein the drill bit tip (12) is manufactured from a material selected from a group consisting of metal, metal alloy, plastic, plastic composite, ceramic, diamond, cubic zirconium, rubber, rubber composite and glass.

3. The improved dental drill bit (10) as described in claim 1, wherein the base (14) is manufactured from a material selected from a group consisting of metal, metal alloy, plastic, plastic composite, ceramic, diamond, cubic zirconium, rubber, rubber composite and glass.

4. The improved dental drill bit (10) as described in claim 1, wherein the shaft (16) is manufactured from a material selected from a group consisting of metal, metal alloy, plastic, plastic composite, ceramic, diamond, cubic zirconium, rubber, rubber composite and glass.

* * * * *